(12) United States Patent
Lower et al.

(10) Patent No.: US 6,808,527 B2
(45) Date of Patent: Oct. 26, 2004

(54) INTRAMEDULLARY NAIL WITH SNAP-IN WINDOW INSERT

(75) Inventors: Jerry L. Lower, Bourbon, IN (US); David W. Overaker, Annandale, NJ (US)

(73) Assignee: DePuy Orthopaedics, Inc., Warsaw, IN (US)

(*) Notice: Subject to any disclaimer, the term of this patent is extended or adjusted under 35 U.S.C. 154(b) by 62 days.

(21) Appl. No.: 10/105,763

(22) Filed: Mar. 25, 2002

(65) Prior Publication Data

US 2002/0103488 A1 Aug. 1, 2002

Related U.S. Application Data

(63) Continuation-in-part of application No. 09/575,764, filed on May 22, 2000, now Pat. No. 6,709,436, which is a continuation of application No. PCT/US00/09582, filed on Apr. 10, 2000.

(51) Int. Cl.⁷ .............................................. A61B 17/72
(52) U.S. Cl. ........................................................ 606/62
(58) Field of Search ............................ 606/53, 60, 62, 606/63, 64, 65, 66–68, 72

(56) References Cited

U.S. PATENT DOCUMENTS

| | | | |
|---|---|---|---|
| 478,118 A | 11/1892 | Casey et al. | |
| 2,136,471 A | 11/1938 | Schneider | |
| 2,987,062 A | 6/1961 | Ellison | |
| 3,272,204 A | 9/1966 | Artandi et al. | |
| 3,463,158 A | 8/1969 | Schmitt et al. | |
| 3,531,561 A | 9/1970 | Trehu | |
| 3,596,656 A | 8/1971 | Kante | |
| 3,636,956 A | 1/1972 | Schneider | |
| 3,739,773 A | 6/1973 | Schmitt et al. | |
| 3,892,646 A | 7/1975 | Phillips et al. | |
| 3,902,497 A | 9/1975 | Casey | |
| 3,918,100 A | 11/1975 | Shaw et al. | |
| 3,937,223 A | 2/1976 | Roth | |
| 3,960,151 A | 6/1976 | Kuhn | |

(List continued on next page.)

FOREIGN PATENT DOCUMENTS

| | | |
|---|---|---|
| DE | 194992304 | 4/1971 |
| EP | 0491983 A1 | 7/1992 |
| FR | 271083504 | 4/1995 |
| SU | 1692566 | 11/1991 |

OTHER PUBLICATIONS

Brochure of Intramedullary Nail.
One–Nail . . . Diaphyseal Fractures.
Ordway, Craig B., Surgical Technique, AIM Titanium Femoral Nail System, New York, pp. 1–11.

(List continued on next page.)

*Primary Examiner*—David O. Reip
*Assistant Examiner*—Jessica R. Baxter
(74) *Attorney, Agent, or Firm*—Maginot Moore & Beck (57) ABSTRACT

An intramedullary nail has a dynamization opening that accommodates and utilizes a dynamization window insert. The dynamization window insert is press-fit into the dynamization opening. The dynamization window insert is oval shaped and includes first and second protrusions that extend from respective surfaces of the dynamization window insert. The dynamization opening is sized to receive the dynamization window insert but compress the protrusions/window insert during insertion. The dynamization opening includes channels or grooves that are sized to accommodate the protrusions and allow the protrusions/window insert to return to an uncompressed state when situated therein. The dynamization opening and window insert cooperate to allow a press fit of the window insert into the dynamization opening with an elastic snap-fit and audible sound.

28 Claims, 9 Drawing Sheets

U.S. PATENT DOCUMENTS

| | | | |
|---|---|---|---|
| 4,146,936 A | 4/1979 | Aoyagi et al. | |
| 4,186,448 A | 2/1980 | Brekke | |
| 4,192,021 A | 3/1980 | Deibig et al. | |
| 4,279,249 A | 7/1981 | Vert et al. | |
| 4,280,233 A | 7/1981 | Raab | |
| 4,292,694 A | 10/1981 | Koeneman | |
| 4,338,926 A | 7/1982 | Kummer et al. | |
| 4,429,690 A | 2/1984 | Angelino-Pievani | |
| 4,457,301 A | 7/1984 | Walker | |
| 4,523,591 A | 6/1985 | Kaplan et al. | |
| 4,550,449 A | 11/1985 | Tunc | |
| 4,612,923 A | 9/1986 | Kronenthal | |
| 4,655,203 A | 4/1987 | Törmälä et al. | |
| 4,733,654 A | 3/1988 | Marino | |
| 4,756,307 A | 7/1988 | Crowninshield | |
| 4,790,302 A | 12/1988 | Colwill et al. | |
| 4,851,008 A | 7/1989 | Johnson | |
| 4,863,475 A | 9/1989 | Andersen et al. | |
| 4,875,474 A | 10/1989 | Border | |
| 4,895,572 A | 1/1990 | Chernoff | |
| 4,898,186 A | 2/1990 | Ikada et al. | |
| 4,911,153 A | 3/1990 | Border | |
| 4,919,666 A | 4/1990 | Buchhorn et al. | |
| 4,943,292 A | 7/1990 | Foux | |
| 4,968,317 A | 11/1990 | Törmälä et al. | |
| 4,973,333 A | 11/1990 | Treharne | |
| 5,057,110 A | 10/1991 | Kranz et al. | |
| 5,057,111 A | 10/1991 | Park | |
| 5,084,050 A | 1/1992 | Draenert | |
| 5,084,051 A | 1/1992 | Törmälä et al. | |
| 5,108,399 A | 4/1992 | Eitenmuller et al. | |
| 5,112,333 A | 5/1992 | Fixel | |
| 5,127,913 A | 7/1992 | Thomas, Jr. | |
| 5,190,546 A | 3/1993 | Jervis | |
| 5,236,431 A | 8/1993 | Gogolewski et al. | |
| 5,275,601 A | 1/1994 | Gogolewski et al. | |
| 5,292,695 A | 3/1994 | Galloway | |
| 5,413,577 A | 5/1995 | Pollock | |
| 5,484,438 A | 1/1996 | Pennig | |
| 5,514,137 A | 5/1996 | Coutts | |
| 5,562,667 A * | 10/1996 | Shuler et al. | 606/64 |
| 5,569,250 A | 10/1996 | Sarver et al. | |
| 5,603,715 A | 2/1997 | Kessler | |
| 5,618,286 A | 4/1997 | Brinker | |
| 5,741,266 A | 4/1998 | Moran et al. | |
| 5,766,174 A * | 6/1998 | Perry | 606/62 |
| 5,769,852 A * | 6/1998 | Branemark | 606/65 |
| 5,776,194 A | 7/1998 | Mikol et al. | |
| 5,792,400 A | 8/1998 | Talja et al. | |
| 5,810,821 A | 9/1998 | Vandewalle | |
| 5,836,949 A | 11/1998 | Campbell, Jr. | |
| 5,855,879 A | 1/1999 | James et al. | |
| 5,868,746 A | 2/1999 | Sarver et al. | |
| 5,871,484 A | 2/1999 | Spievack et al. | |
| 5,895,390 A | 4/1999 | Moran et al. | |
| 5,928,267 A | 7/1999 | Bonutti et al. | |
| 5,935,127 A | 8/1999 | Border | |
| 6,004,323 A | 12/1999 | Park et al. | |
| 6,053,918 A * | 4/2000 | Spievack | 606/64 |
| 6,106,528 A * | 8/2000 | Durham et al. | 606/62 |
| 6,228,086 B1 * | 5/2001 | Wahl et al. | 606/67 |
| 6,488,684 B2 * | 12/2002 | Bramlet | 606/62 |
| 2002/0151898 A1 * | 10/2002 | Sohngen et al. | 606/62 |
| 2003/0018336 A1 * | 1/2003 | Vandewalle | 606/67 |

OTHER PUBLICATIONS

Biomet Inc., Vector Intertrochanteric Nail, Version Two, 18 pages, 1995. USA.

Biomet Inc., Biomet Retrograde Femoral Nail Surgical Technique, 12 pages, 1995. USA.

System Introduction, The Titanium Unreamed Tibial Nail System.

Biomet Inc., Biomet Retrograde Femoral Nail, 6 pages, 1995. USA.

Biomet Inc., UNIFLEX® Hummeral Nail Surgical Technique, 14 pages, 1997. USA.

Biomet Inc., UNIFLEX® Hummeral Nail Surgical Technique, 18 pages, 1996. USA.

Biomet Inc., Titanium Femoral Interlocking Nail, 16 pages, 1995. USA.

Biomet Inc., Vector Interochanteric Nail, Version One, 16 pages, 1995. USA.

Biomet Inc., UNFLEX™ Tibial Nail System, 4 pages, 1995. USA.

Biomet Inc., UNIFLEX® Family Nailing System, 16 pages, 1995. USA.

Orthopaedic Equipment Co., Inc. "They Through He Wouldn't Make the Tournament", 1 page. 1976.

McKellp et al., *Develpoment and Clinical Performance of a Reversible Titanium Alloy Femoral Intramedullary Nail*, 16 pages, 1991. USA.

Ferguson, Wyss and Pichora, "*Finite Element Stress Analysis of a Hybrid Fracture Fixation Plate*", Medical Engineering & Physics, vol. 18, No. 3, pp. 241–250, Apr., 1996.

Yeadon, Foux, Uhthoff, and Russell, "*Influence of Axially Flexible Plates on Bone Healing: A Biomechanical Study in Canine Femora*", CMBES 20 CCGB, pp. 34–35, 1994.

Simon, Ricci, and Di Cesare, "*Bioresorable Fracture Fixation in Orthopedics: A Comprehensive Review. Part II. Clinical Studies*", American Journal of Orthopedics, pp. 754–762, Nov., 1997.

Kato, Latta, and Malinin, "*The Weakest link in the Bone–Plate–Fracture System: Changes with Time*", Clinical and Laboratory Performance of Bone Paltes, ASTM STP 1217, ed. By Harvey and Games, pp. 84–94, 1994.

Hazre and Lin, "*Theoretical Strength Comparison of Bioabsorbable (PLLA) Plates and Conventional Stainless Steel and Titanium Plates Used in Internal Fracture Fixation*", Clinical and Laboratory Performance of Bone Plates, ASTM STP 1217, ed. By Harvey and Games, pp. 53–64, 1994.

Räihä, "*Biodegradable Implants as Intramedullary Nails. A Survey of Recent Studies and an Introduction to their Use*", Clinical Materials, vol. 10, pp.35–39, 1992.

Foux, Yeadon, and Uhthoff, "*Improved Fracture Healing with Less Rigid Plates: A biomechanical Study in Dogs*", Clinical Orthopaedics and Related Research, ed. Brighton, No.339, pp. 232–245, 1997.

* cited by examiner

INTRAMEDULLARY NAIL WITH SNAP-IN WINDOW INSERT

The present U.S. non-provisional patent application is a continuation-in-part and thus claims priority to and/or the benefit of co-pending U.S. patent application Ser. No. 09/575,764, filed May 22, 2000 now U.S. Pat. No. 6,709,436 and entitled Non-Metal Spacers For Intramedullary Nail, which is a continuation of PCT application number PCT/US00/09582, filed Apr. 10, 2000.

TECHNICAL FIELD OF THE INVENTION

The present invention relates generally to intramedullary nails used for treatment of a fracture of a bone having a medullary canal extending longitudinally within the bone and, more particularly, to the structure of the intramedullary nail and/or spacer and methods for anchoring the intramedullary nail and spacers with respect to one or more fragments of the fractured bone.

BACKGROUND OF THE INVENTION

Intramedullary nails are used by orthopaedic surgeons to treat fractures involving long bones such as the femur, humerus, tibia, fibula, and others. In such treatment, the medullary canal of the various fragments or pieces of the fractured bone is drilled out, reamed, or otherwise opened from one end. The intramedullary nail is then longitudinally placed in the medullary canal to contact at least two of the fragments, i.e. such that the nail extends on both sides of the fracture. As used herein, the term "fragment" refers to a portion of a fractured bone regardless of whether the fracture is complete. When implanted, the intramedullary nail supports and strengthens fragments of the fractured bone during healing of the fracture.

Various types of intramedullary nails are well known within the medical device arts, and several different methods have been used to attach the intramedullary nail to and within the bone. As an example, in U.S. Pat. No. 4,338,926 to Kummer et al., an intramedullary nail is shown that provides a compressive force radially outward on an interior wall of the cortex structure surrounding the intramedullary nail. The compressive force secures the Kummer intramedullary nail within the medullary canal of the fragments. Similarly, in U.S. Pat. No. 5,514,137 to Coutts, cement is injected through a cannula in an intramedullary nail to the bone. Other intramedullary nails employ a more secure and mechanically positive attachment to the bone, such as through the use of one or more bone fasteners that extend generally transversely to the longitudinal axis of the intramedullary nail and through the cortex of the bone. The bone fasteners is received within a receiving recess or through-hole within the intramedullary nail to secure the intramedullary nail relative to the bone fastener. In a transverse attachment, the receiving opening of the intramedullary nail defines an axis that is at an angle to the longitudinal axis of the nail (commonly at 45° and 90° angles), and the bone fastener is advance on this receiving opening axis. U.S. Pat. No. 4,733,654 to Marino, U.S. Pat. No. 5,057,110 to Kranz et al., U.S. Pat. No. 5,127,913 to Thomas, Jr., U.S. Pat. No. 5,514,137 to Coutts (proximal end) and others disclose such a transverse bone fastener attachment in a bicortical attachment. U.S. Pat. No. 5,484,438 to Pennig shows a nail design with a recess that permits only unicortical attachment. The subject invention particularly pertains to intramedullary nails that utilize bone fasteners transversely through the cortex for attachment.

Problems may arise when attaching an intramedullary nail to a fragment with a bone fastener. It is occasionally difficult for the surgeon to properly align the bone fastener and/or a hole for the bone fastener with the receiving opening in the intramedullary nail. Part of the alignment problems is simply due to difficulty in aligning the bone fastener with the receiving opening when the receiving opening is within the bone. Additionally, the intramedullary nail may be slightly bent or distorted during insertion thereof into the medullary canal. Such bending and/or distortion may be desired in some instances so that the shape of the inserted intramedullary nail better matches the particular shape of the medullary canal for a particular patient.

Regardless of whether intended or unintended, such bending or distortion of the intramedullary nail creates further alignment errors between the bone fastener and/or a hole for the bone fastener and the receiving opening on the nail. Four types of alignment errors can be identified: (a) in transverse displacement (e.g., when the axis of the bone fastener is in the same transverse plane as the receiving opening in the intramedullary nail but does not intersect the axis of the intramedullary nail); (b) in longitudinal displacement (i.e., when the bone fastener is at a different longitudinal location than the receiving opening in the intramedullary nail); (c) in longitudinal angular misalignment (i.e., when the axis of the receiving opening and the axis of the bone fastener are at different angles relative to the longitudinal axis of the intramedullary nail); and (d) in transverse angular misalignment (i.e., when the axis of the receiving opening and the axis of the bone fastener are in the same transverse plane but at different radial positions relative to the intramedullary nail.

In view of the above, various types of jigs have been proposed to reduce alignment errors, such as shown in U.S. Pat. No. 4,733,654 to Marino and U.S. Pat. No. 5,776,194 to Mikol et al. Such jigs may be temporarily attached to the proximal end of the intramedullary nail to help align the bone fastener and/or the drill to the receiving opening in the intramedullary nail. While such jigs are helpful, the jigs become less reliable as distance from the proximal end of the intramedullary nail increases, particularly if any bending of the intramedullary nail has occurred. Additional solutions are needed, especially for attaching the distal end of the intramedullary nail to a distal fragment.

Another method to reduce such alignment problems is to locate the receiving opening(s) in-situ, such as through an x-ray or the use of magnets as taught in U.S. Pat. No. 5,127,913 to Thomas, Jr. Such methods are not typically preferred by surgeons in as much as the methods require significant additional time and effort during the orthopaedic surgery, to the detriment of the patient.

A third method to reduce such alignment problems is to drill the receiving opening into the intramedullary nail only after the intramedullary nail is placed into the bone, allowing the receiving opening to be formed at a range of locations. Such in-situ drilling is disclosed in U.S. Pat. No. 5,057,110 to Krans et al., wherein a tip section of the intramedullary nail is formed of a bioresorbable material. Bioresorbable materials, however, are not as strong as metals, leading to an intramedullary nail that is weaker than desired and has a weaker attachment than desired.

Further problems with intramedullary nails occur during placement of the intramedullary nail. For minimal damage to cortical tissue of the bone and most beneficial to healing, both the hole that is drilled in the medullary canal for the intramedullary nail and then the intramedullary nail itself, need to be precisely located and secured with respect to the medullary canal.

Additional problems with intramedullary nails occur due to the healing requirements of a bone with respect to the strength and rigidity of the intramedullary nail. U.S. Pat. No. 4,756,307 to Crowninshield and U.S. Pat. No. 4,338,926 to Kummer et al. disclose intramedullary nails with bioresorbable portions to weaken the mail relative to the bone over time. These intramedullary nails, however, forsake the use of a transverse bone fastener to achieve the benefit of the bioresorbable portions.

It would thus be advantageous to provide an intramedullary nail that overcomes the above-noted shortcomings. It would be further advantageous to provide an intramedullary nail and related portions and/or components that overcome the above-noted and other shortcomings.

SUMMARY OF THE INVENTION

The subject invention is an intramedullary nail for treatment of a fracture of a bone by placement of the intramedullary nail within the medullary canal of the fractured bone. The intramedullary nail is formed with at least one opening in an exterior side that is adapted to receive a spacer or window insert of a non-metal material. The opening and window insert have cooperating structures that provide a spring type elastic fit, snap-fit, and/or interference fit of the window insert within the opening. The nail is used with a bone fastener such as a bone screw that is advanced transversely through the bone and into the spacer, preferably in a bicortical attachment with the bone.

The bone fastener is smaller across than the window insert so that the window insert spaces the bone fastener relative to the metal structure of the intramedullary nail. The opening may have a longitudinal length that is different from its width, while the bone fastener has a circular length. Because the bone fastener is smaller across than the opening and the window insert, a larger error in placement of the bone fastener is permissible.

In one form, there is provided an intramedullary nail for treatment of a fracture of a bone having a medullary canal extending longitudinally. The intramedullary nail includes a nail structure and a window insert. The nail structure has a longitudinal nail body defining a distal end and a proximate end. The nail body has a dynamization opening in one of the distal end and the proximate end. The dynamization opening has a first interference receptor disposed in a wall of the dynamization opening and a second interference receptor disposed in the wall. The window insert is formed of a non-metal material and is adapted to be inserted into the dynamization opening. The window insert has a window insert body having a first interference extending from a first surface of the window insert body and a second interference extending from a second surface of the window insert body. The first and second interferences are adapted to be received in the first and second interference receptors of the dynamization opening respectively upon insertion of the window insert into the dynamization opening.

In another form, there is provided an intramedullary nail for treatment of a fracture of a bone having a medullary canal extending longitudinally. The intramedullary nail is defined by a longitudinal nail body. The longitudinal nail body defines a distal end and a proximate end, with the nail body having a dynamization opening extending through the nail body at one of the distal end and the proximate end essentially transverse to a longitudinal axis of the nail body. The dynamization opening is defined by an oval wall with the oval wall having a first groove positioned essentially parallel to the longitudinal axis and a second groove disposed diametrically opposite the first groove and essentially parallel to the longitudinal axis. The dynamization window insert is formed of a non-metal material and is adapted to be inserted into the dynamization opening. The window insert has an oval window insert body having a first rail extending a first distance from a first surface of the window insert body and a second rail extending a second distance from a second surface of the window insert body. The first and second rails are adapted to be received in the first and second grooves of the dynamization opening respectively upon insertion of the dynamization window insert into the dynamization opening.

In yet another form, there is provided a window insert for a dynamization opening of an intramedullary nail. The window insert has an oval body defining a top and bottom surface, a first and second side surface, and a first and second curved side. A first rail is disposed on the first side and extends a first distance therefrom. A second rail is disposed on the second side and extends a second distance therefrom.

In still another form, there is provided a method of retaining bone fragments. The method includes the steps of: (a) placing a dynamization window insert in a dynamization opening of an intramedullary nail, the intramedullary nail having a longitudinal nail body defining a distal end and a proximate end, the dynamization opening extending through the nail body at one of the distal end and the proximate end essentially transverse to a longitudinal axis of the nail body, the dynamization opening defined by an oval wall, the oval wall having a first groove positioned essentially parallel to the longitudinal axis and a second groove disposed diametrically opposite the first groove and essentially parallel to the longitudinal axis, the dynamization window insert formed of a non-metal material and adapted to be inserted into the dynamization opening, the window insert having an oval window insert body having a first rail extending a first distance from a first surface of the window insert body and a second rail extending a second distance from a second surface of the window insert body, said first and second rails adapted to be received in the first and second grooves of the dynamization opening respectively upon insertion of the dynamization window insert into the dynamization opening; (b) placing the intramedullary nail through the bone fragments, and (c) inserting a bone fastener through the dynamization window insert.

In a yet further form, there is provided a bone support assembly for treatment of a bone. The bone support assembly includes a bone support implant formed of a non-resorbable material, and a first window insert formed of a non-metal material. The bone support implant has a first opening defined therein. The first opening has a first opening shape including a narrow portion adjacent an outer surface of the bone support implant and a wider portion more interior the bone support implant. The first window insert has outer dimensions that correspond to the first opening. The first window insert has a first section that mates with the narrow portion of the first opening. The first window insert has a second section wider than the first section that mates with the wider portion of the first opening more interior of the bone support implant. In this manner, the second section of the first window insert is wider than the narrow portion of the first opening and serves to positively secure the first window insert in the first opening with an interference fit.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

While the invention Is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention as defined by the appended claims. As well, reference should be made to the parent case of the present case (i.e. U.S. nonprovisional patent application Ser. No. 09/575,764, filed May 22, 2000 and entitled Non-Metal Spacers For Intramedullary Nail, which is a continuation of PCT application No. PCT/US00/09582, filed Apr. 10, 2000), the specification of which is hereby specifically incorporated by reference. Additionally, reference should be made to U.S. patent application Ser. No. 09/289,324, filed Apr. 9, 1999, entitled Intramedullary Nail With Non-Metal Spacers, now issued as U.S. Pat. No. 6,296,645, the specification of which is hereby specifically incorporated by reference.

Figure 1:
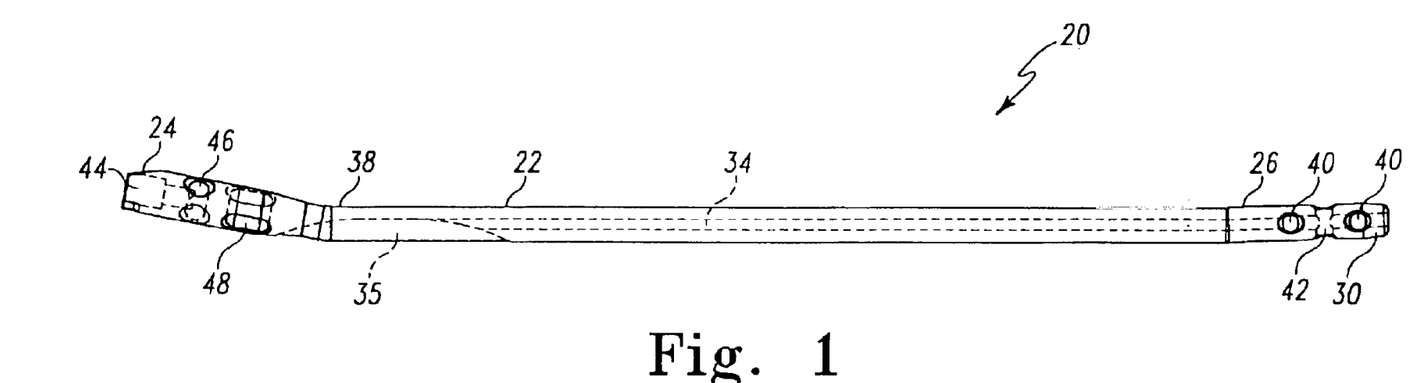
FIG. 1 is a perspective view of an exemplary intramedullary nail in accordance with the principles of the subject invention.
Figure 2:
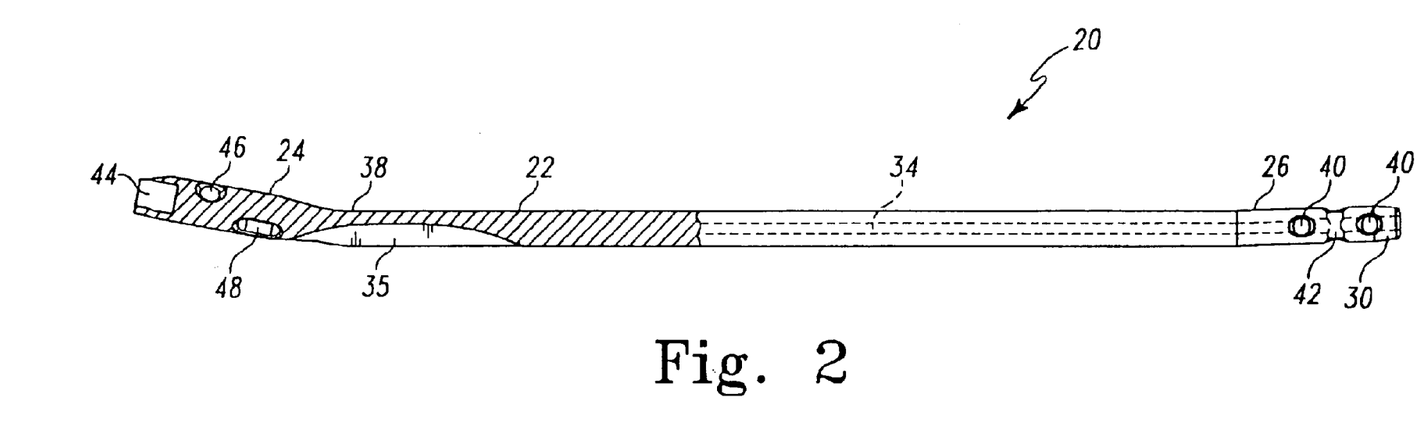
FIG. 2 is a perspective view of the exemplary intramedullary nail of FIG. 1 in partial sectional.

Referring now to FIGS. 1 and 2 there is depicted an exemplary intramedullary nail generally designated 20, in accordance with the principles of the subject invention. The intramedullary nail 20 has a body or shaft 22 that defines a proximal end 24 and a distal end 26, with "proximal" and "distal" being defined in accordance with the direction the nail 20 is intended to be inserted into a bone. As known in the art, the dimensions of the proximal end 24, the distal end 26, and the body 22 may be selected based on the required strength of the intramedullary nail 20 and the intended use of the intramedullary nail 20. The intramedullary nail 20 depicted in the various figures is generally sized and shaped for treating a fracture toward the middle of an otherwise healthy adult human femur. If desired, the intramedullary nail 20 may be included in a kit having various sizes of intramedullary nails to accommodate the femurs of variously sized patients, and/or having various sizes of intramedullary nails to fit various types of femoral bone conditions or various types of femoral fractures, and/or further having various sizes of intramedullary nails to fit various other bones. For instance, the length of the intramedullary nail 20 may be selected as needed between about 10 to 20 inches.

The distal end 26 may include a tip 30 having, for instance, a conical or partially conical profile. The conical profile of the tip 30 aids in inserting the intramedullary nail 20 into the medullary canal of a bone. The body may be generally of constant diameter. The proximal end 24 may include a portion of larger diameter than the body 22.

As known in the art, the intramedullary nail 20 has an overall cross-sectional shape selected based on the intended use. For the femoral intramedullary nail 20, the cross-sectional shape may be generally circular to match the shape of the medullary canal of a healthy femur. For instance, the body 22 may be generally formed with an outside diameter of 0.394 inches.

A cannula 34 preferably extends the internal length of the intramedullary nail 20. The cannula 34 facilitates insertion and alignment of the intramedullary nail 20 within the medullary canal. The cannula 34 may be formed in various manners, but is typically formed by drilling longitudinally the length of the nail 20 through a lateral opening 35. The cannula 34 receives a guide wire (not shown) during insertion of the intramedullary nail 20 into the medullary canal. The guide wire has to be thick enough to provide the requisite strength and rigidity for placement into the bone, and the cannula 34 must be large enough to receive the guide wire and permit longitudinal travel of the intramedullary nail 20 along the guide wire. Conversely, because a larger cannula 34 detracts from the strength of the intramedullary nail 20, the cannula 34 should be as small as required for travel over the guide wire. The preferred guide wire is circular in cross-section, as well as the cannula 34. For instance, the cannula 34 may be about 0.156 inches in diameter. With a body 22 of 0.394 inch (10 mm) diameter, the cannula 34 leaves a wall thickness for the body 22 of about 0.118 inches.

The preferred intramedullary nail 20 includes a radius bend 38 in the body 22, generally intended to match the anterior-posterior bend of a healthy femur. The bend 38 may have a large radius in relation to the length of the intramedullary nail 20, such as a bend with a radius of 2 to 10 times the length of the intramedullary nail 20, or may be a small radius in relation to the length of the intramedullary nail 20, such as a bend with a radius of less than 2 times the length of the intramedullary nail 20.

Other than the cannula 34 being open from only one side of the shaft 28, the intramedullary nail 20 is preferably symmetrical about a bisecting anterior-posterior plane. This allows the intramedullary nail 20 to be used in either the right or left femur while still maintaining the bend 38 appropriate for the curvature of the femur.

The body 22 is formed of a structurally strong biocompatible material as known in the art. For instance, the body 22 can be formed of a single piece of metal, with the preferred metal being titanium, such as a Ti-6AL-4V ELI titanium per ASTM F-136.

The distal end 26 is preferably formed with one or more through-holes 40 to facilitate attachment to a distal bone fragment. For instance, the distal end 26 may include two through-holes 40 each having a central axis that is positioned perpendicular to the cannula 34. While not shown, the through-holes 40 may extend at an angle relative to a longitudinal axis of the body 22. The through-holes 40 allow attachment to a bone fragment such as a femoral fragment by bicortical attachment. Alternatively, or in conjunction with the through-holes 40, an annular recess 42 is provided in the distal end 26 to permit attachment to the distal end of a bone.

The proximal end 24 of the intramedullary nail 20 is formed with a through-hole 46 to facilitate attachment to a proximal bone fragment. The through-hole 46 has a central axis that is perpendicular to a longitudinal axis of the proximal end 24 as the longitudinal axis of the proximal end 24 is angled relative to the longitudinal axis of the body 22. The proximal end 24 may further include structure to facilitate attachment of a drilling or alignment jig (not shown) as known in the art for placement of bone fasteners relative to the intramedullary nail 20. For instance, a proximal opening 44 aligned along the longitudinal axis of the proximal end 24 may be used to receive an end of a jig in a mating relationship. Those skilled in the art will appreciate that numerous other structures could be equivalently used to temporarily hold the jig relative to the intramedullary nail 20.

The proximal end 24 of the body 22 includes a dynamization opening 48 that extends therethrough. The opening 48 is referred to as a "dynamization" opening because, when used in conjunction with a properly dimensioned bone fastener (see FIG. 13) and with a window insert or spacer 70 (see e.g. FIGS. 5–8), formed of a polymer and/or bioresorbable material, the proportion of stress carried by the intramedullary nail 20 relative to stress carried by the healing bone across the fracture site dynamically changes as a function of time.

It should be appreciated that the single dynamization opening 48 permits only unicortical attachment. Therefore, two dynamization openings may be provided (see FIG. 13) to permit bi-cortical attachment. The two dynamization openings would be provided on opposite sides of the body 22. Of course, additional dynamization openings or sets of dynamization openings may be provided. In all cases, the structure and function of each dynamization opening is the same in accordance with the subject principles.

Figure 3:
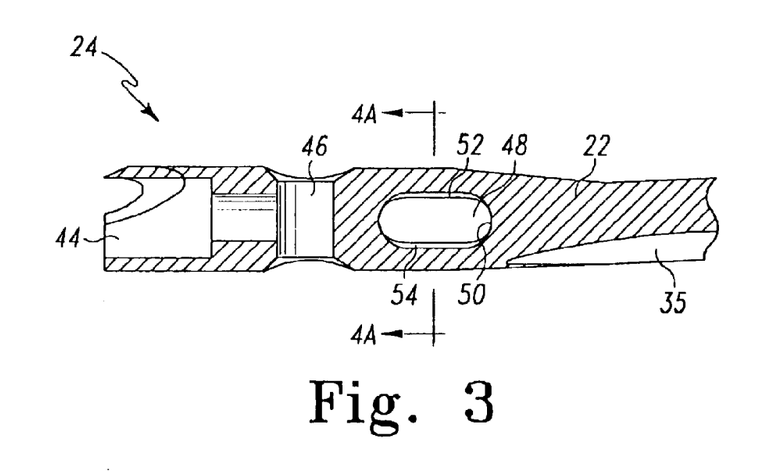
FIG. 3 is an enlarged fragmentary sectional view of the intramedullary nail of FIG. 2.

Referring now to FIG. 3, the proximal end 24 of the intramedullary nail 20 is shown in sectional particularly showing the dynamization opening 48. An oval wall 50 that extends through the body 22 defines the dynamization opening 48. A first channel or groove 52 is formed in a first elongated wall portion 53 of the oval wall 50. The first channel 52 preferably extends an entire length of the elongated wall portion 53, but not necessarily. A second channel or groove 54 is formed in a second elongated wall portion 55 of the oval wall 50. The second channel 54 preferably extends an entire length of the elongated wall portion 55, but not necessarily. Additionally, the first and second channels 52 and 54 are preferably the same length and overall dimension. If the dynamization opening intersects (or cuts through) the cannula of the intramedullary nail (which is not the case in FIG. 3), the first and second channels 52 and 54 each preferably extend respectively along the first and second elongated wall portions from where the cannula intersects the wall portion of the dynamization opening to the opposite side of the wall portion where the cannula intersects the dynamization opening 48. It should be appreciated that the designations first and second are arbitrary. As such, the first may be the second and the second may be the first. Other designations may be used as appropriate.

Figure 4A:
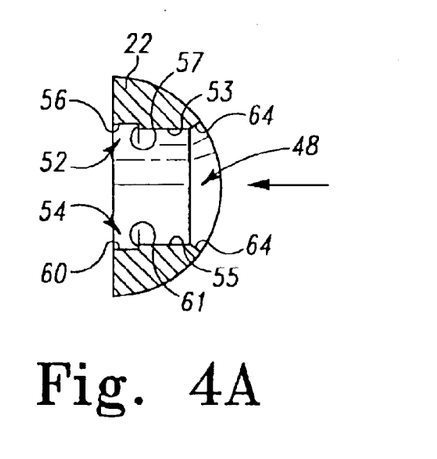
FIGS. 4A and 4B are an enlarged sectional views of the intramedullary nail of FIG. 3 taken along line 4A—4A thereof.
Figure 4B:
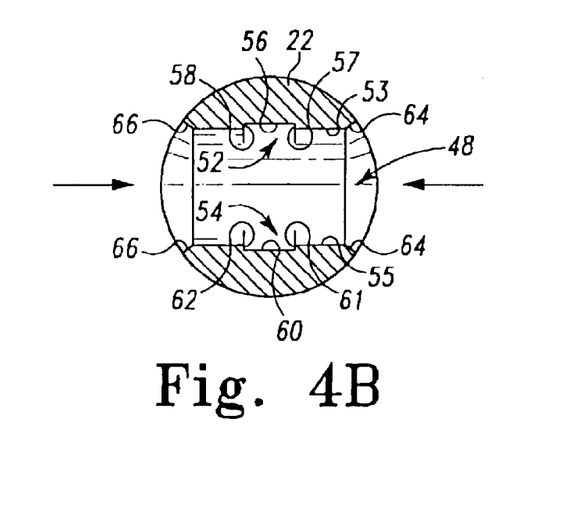
Figure 5:
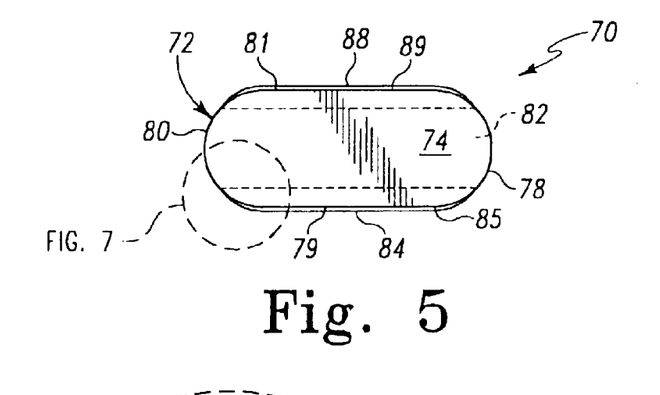
FIG. 5 is an enlarged top plan view of an exemplary window insert for the intramedullary nail.

Referring to FIG. 4A, there is depicted a cross section of the intramedullary nail 20 taken along the middle of the dynamization opening 48, particularly along line 4A—4A of FIG. 3. Since FIG. 4A only shows half of the cross-section, reference is also made to FIG. 4B which shows a full cross section of the intramedullary nail 20 taken along the middle of the dynamization opening 48. The first channel 52, in one form, is defined by an elongated wall 56 bounded on one side by a first side wall 57 and on another side by a second side wall 58. The walls 56, 57, and 58 define a rectangular shape for the first channel 52. It should be appreciated that the first channel 52 may take shapes other than rectangular such as rounded or arcuate, square, or the like. The second channel 54, in one form, is defined by an elongated wall 60 bounded on one side by a first side wall 61 and on another side by a second side wall 62. The walls 60, 61, and 62 define a rectangular shape for the second channel 54. It should be appreciated that the second channel 54 may take shapes other than rectangular such as rounded or arcuate, square, or the like. Preferably, the first and second channels 52 and 54 have the same shape, which is rectangular.

Access to the dynamization opening, represented by the arrows (which also represent the direction of insertion of a dynamization window insert 70, see e.g. FIGS. 5–8, into the dynamization opening 48) is characterized by an angled, chamfered, or tapered wall 64 on one side of the dynamization opening 48 and by an angled, chamfered, or tapered wall 66 on another side of the dynamization opening 48. The angled walls 64 and 66 each extend about the entire periphery of the respective sides of the dynamization opening 48. As explained more fully below, the angled walls 64 and 66 assist in receiving or introducing the window insert 70 (depending on the side of insertion of the window insert 70) into the dynamization opening 48.

Figure 12:
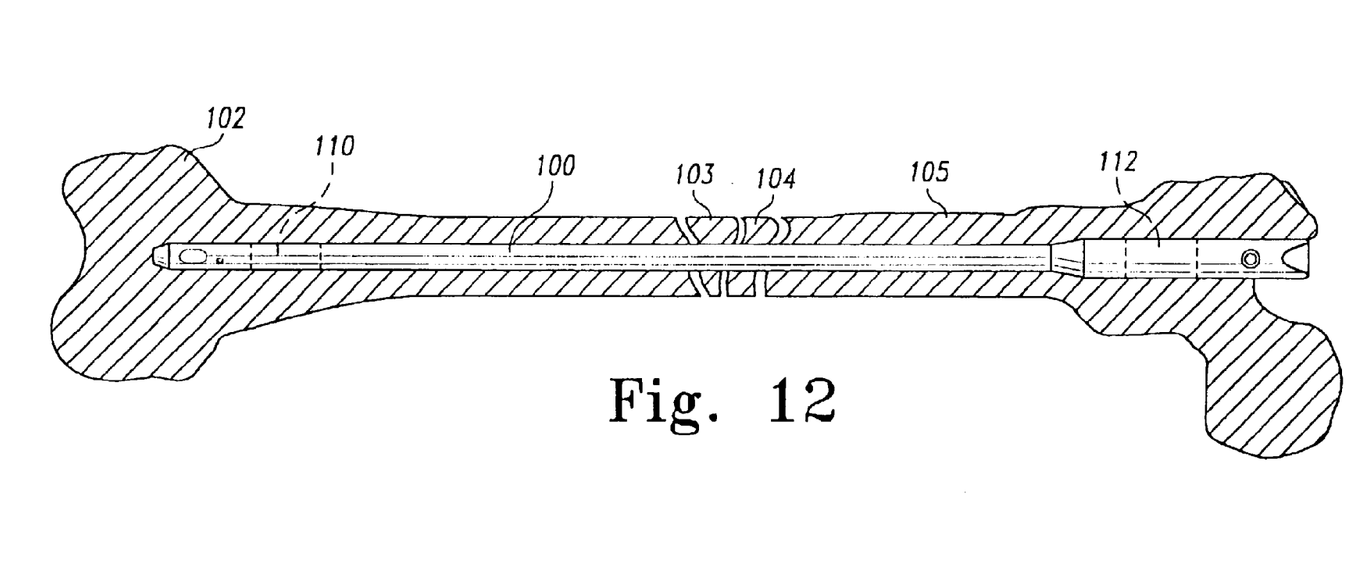
FIG. 12 is a front plan view of a fractured bone in sectional with an intramedullary nail inserted therein.
Figure 13:
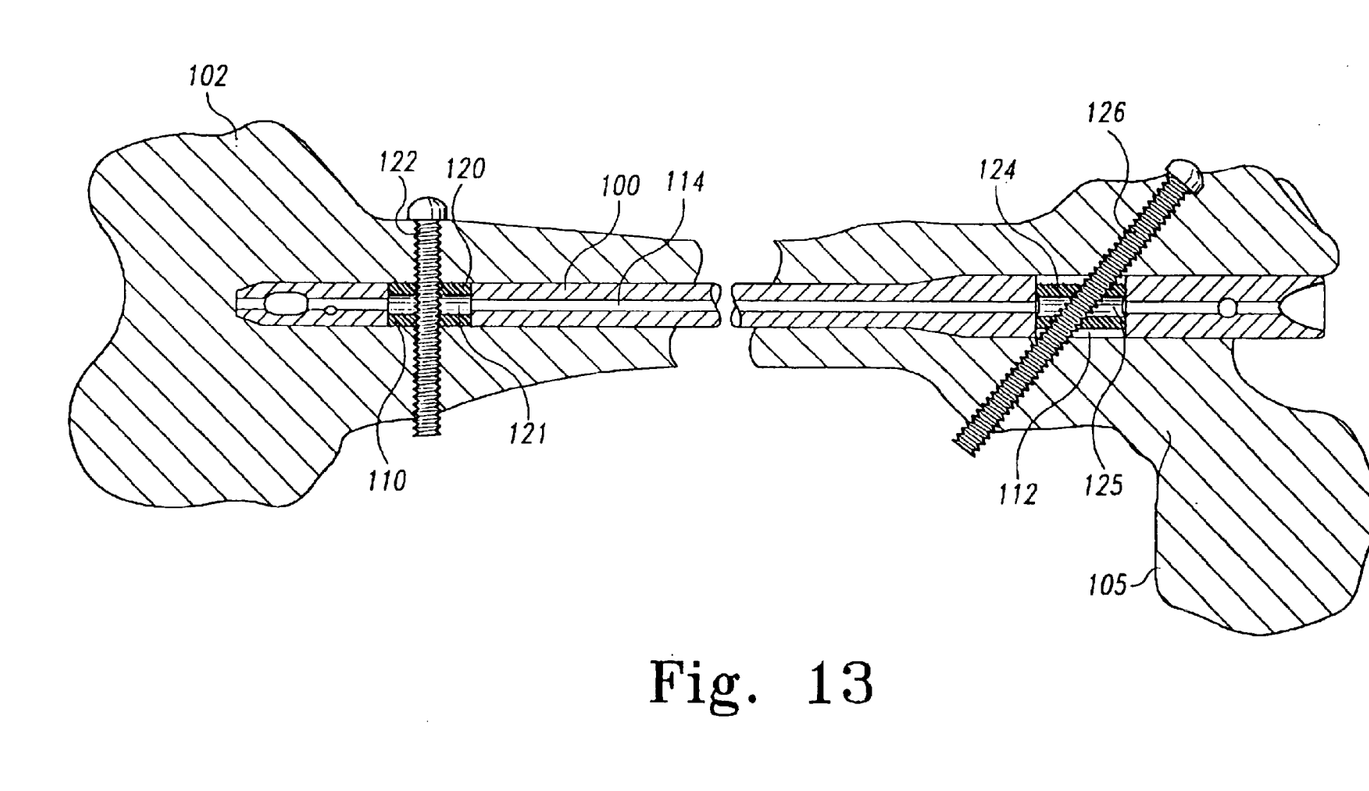
FIG. 13 is a longitudinal sectional view of two bone fragments of a fractured bone having an intramedullary nail and window insert structure inserted therein, particularly with bone fasteners extending through the bone fragments and the respective windows inserts.

Referring now to FIGS. 5–8 there is depicted an exemplary window insert in accordance with the principles of the subject invention that is generally designated 70. The window insert 70 is configured to be received in the dynamization opening 48 and particularly any and all dynamization openings in the intramedullary nail. During use of the intramedullary nail 20 as shown in FIGS. 12 and 13, and explained more fully below, a bone fastener is positioned into the opening 48 through the window insert 70. The window insert 70 spaces the bone fastener relative to the intramedullary nail 20 (and the dynamization opening 48). Force is transmitted between the intramedullary nail 20 and the bone fastener primarily as a compressive load on a portion of the window insert 70.

The window insert 70 is formed of a non-metal material, preferably a bioresorbable material. The term "bioresorbable" as used herein refers to any biocompatible material that dissolves or degrades over time after implantation into the human body. Among others, possible bioresorbable materials includes polymers and copolymers, glycolic acid, lactic acid, aminocaproic acid, lactides, desoxazon, hydroxybutric acid, hydroxyvaleric acid, hydroxymethacrylate, peptides, polyesters of succinic acid and cross-linked hyaluronic acid, or even a biologically absorbable hydroxyapatite or tricalcium phosphate. The preferred bioresorbable material is a polylactic acid ("PLA"), that provides a strong material for the window insert 70. The compressibility of the PLA material shows little change over the first few weeks of implantation, but then increases linearly over the next few months until resorption to the point where the material will no longer support a load. With the preferred PLA material, full resorption will typically occur within about two to five years. If no bioresorption is desired, the non-metal material may be any other polymer commonly used in medical implants, such as a preferred non-metal non-resorbable material of a ultra-high molecular weight polyethylene ("UHMWPE").

The dynamization opening 48 and the dynamization window insert 70 are shaped and/or configured based on the required strength and the desired dynamization characteristics for the intramedullary nail 20. In the preferred embodiment as shown in the figures, both the dynamization opening 48 and the window insert 70 are oval shaped. Particularly, both the dynamization opening 48 and the window insert 70 are oval shaped with elongated sides.

With respect to the window insert 70, the window insert 70 is defined by a body 72 of an appropriate material as explained above. The body 72 includes a top surface or wall 74 and a bottom surface or wall 76. The top and bottom surfaces 74 and 76 are essentially flat and define planes that are essentially parallel. It should be appreciated that the designation or nomenclature of top and bottom are arbitrary. The body 72 also includes a front side surface or wall 79 and a back side surface or wall 81 disposed between the top and bottom surfaces 74 and 76. The front and back side surfaces 79 and 81 essentially define planes that are essentially parallel. Again, it should be appreciated that the designation or nomenclature of front and back are arbitrary. A first rounded end surface or wall 78 is disposed between the top and bottom surfaces 74 and 76, and the front and back surfaces 79 and 81, at one end of the body 72, while a second rounded end surface or wall 80 is disposed between the top and bottom surfaces 74 and 76, and the front and back surfaces 79 and 81, at another end of the body 72.

A cannula 82 extends through the body 72 from one end surface 78 to the other end surface 80. The cannula 82 is preferably centrally disposed in the body 72 and thus aligns with a cannula of the intramedullary nail 20 when the intramedullary nail 20 has a cannula and the dynamization window insert intersects or cuts through the cannula. The cannula 82 is preferably sized to the dimensions of the cannula of the nail.

Figures 6, 8:
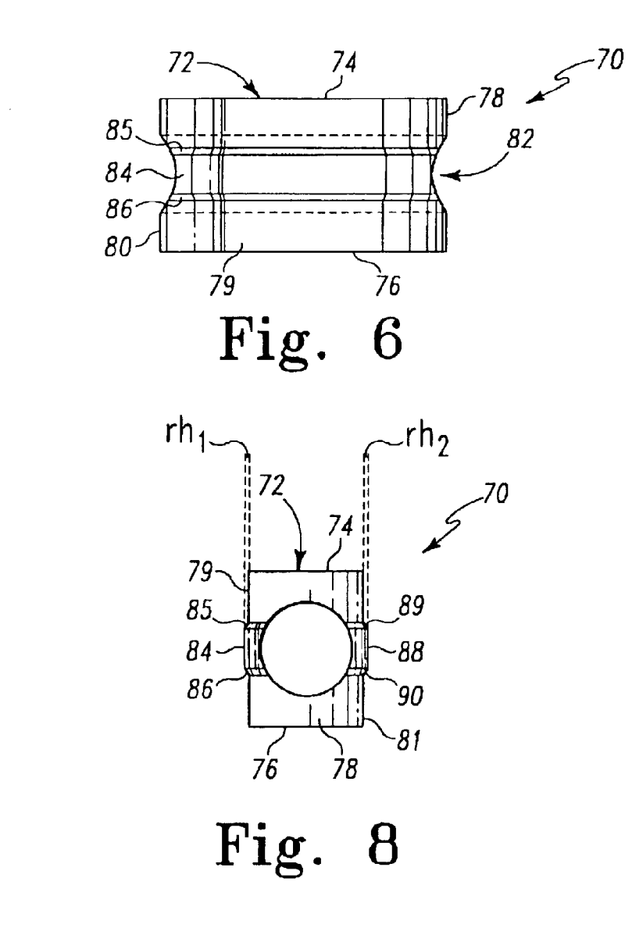
FIG. 6 is an enlarged front plan view of the window insert of FIG. 5.
FIG. 8 is an enlarged side plan view of the window insert of FIG. 5.
Figure 7:
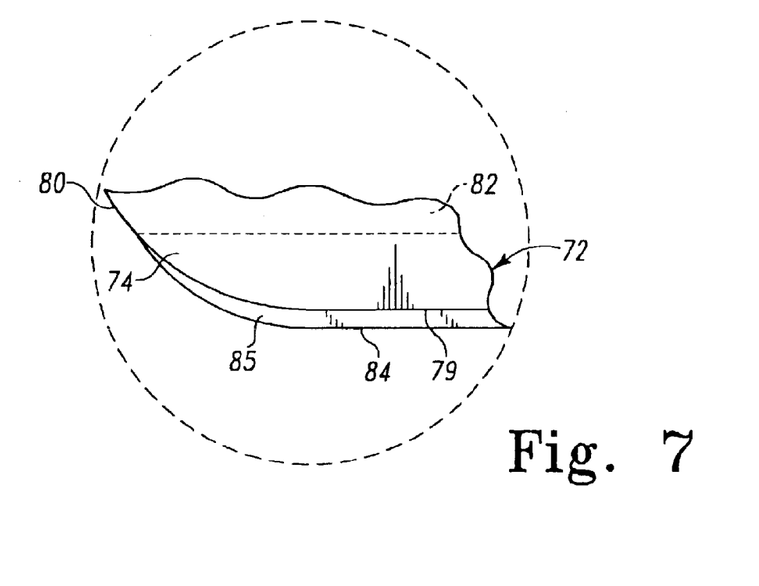
FIG. 7 is a fragmentary view of the window insert of FIG. 5.

The front surface 79 includes a protrusion, rail, ledge, or the like 84 that preferably, but not necessarily, extends from the first end surface 78 to the second end surface 80. The rail 84 is raised relative to the front surface 79 and joins the front surface 79 at a top end by a chamfer, taper, or angled surface 85, and at a bottom end by a chamfer, taper, or angled surface 86. As best seen in FIG. 8, the rear surface 81 also includes a protrusion, rail, ledge, or the like 88 that preferably, but not necessarily, extends from the first end surface 78 to the second end surface 80. The rail 88 is raised relative to the rear surface 81 and joins the rear surface 81 at a top end by a chamfer, taper, or angled surface 89, and at a bottom end by a chamfer, taper, or angled surface 90. In FIG. 7, it is best shown how the rail 84, and particularly the angled surface 85 joins the end surface 80. This is exemplary of both rails 84 and 88 and each of their respective angled surfaces 85, 86 and 89, 90.

In accordance with an aspect of the subject invention, the rail 84 is raised a distance ($rh_1$, or rail height 1) relative to the front surface 79. In particular, the end surface of the rail 84 extends a distance, $rh_1$, from or relative to the front surface 79. In like manner, the rail 88 is raised a distance ($rh_2$ or rail height 2) relative to the rear surface 81. In particular, the end surface of the rail 88 extends a distance, $rh_2$, from or relative to the rear surface 81. The window insert material determines the distances (or interferences) $rh_1$ and $rh_2$ and, more particularly, determines a range of distances for each rail height $rh_1$ and $rh_2$. With the material PLA, the distance $rh_1$ is preferably a minimum of 0.003 inches (0.003") to a maximum of 0.005 inches (0.005") relative to the front surface 79, while the distance $rh_2$ is preferably a minimum of 0.003 inches (0.003") to a maximum of 0.005 inches (0.005") relative to the rear surface 81. In this case, the overall distance that the rails 84 and 88 extend from the surfaces 79 and 81 ranges from 0.006 inches (0.006") to 0.010 inches (0.010"). Depending on the composition of the window insert, the individual rail height and the total rail height will be variable for optimum compression and uncompression of the rails during insertion of the window insert into the dynamization opening. In all cases, however, the total rail height allows the compression thereof during insertion of the window insert in to the dynamization opening and the uncompressing thereof when reaching the dynamization opening channels (interference receptors). Such distance may be considered an interference distance or simply interference. As explained more fully below and in accordance with an aspect of the subject invention, such interference interacts with the dimensions of the dynamization opening 48 including the first and second channels 52 and 54 thereof.

Figure 9:
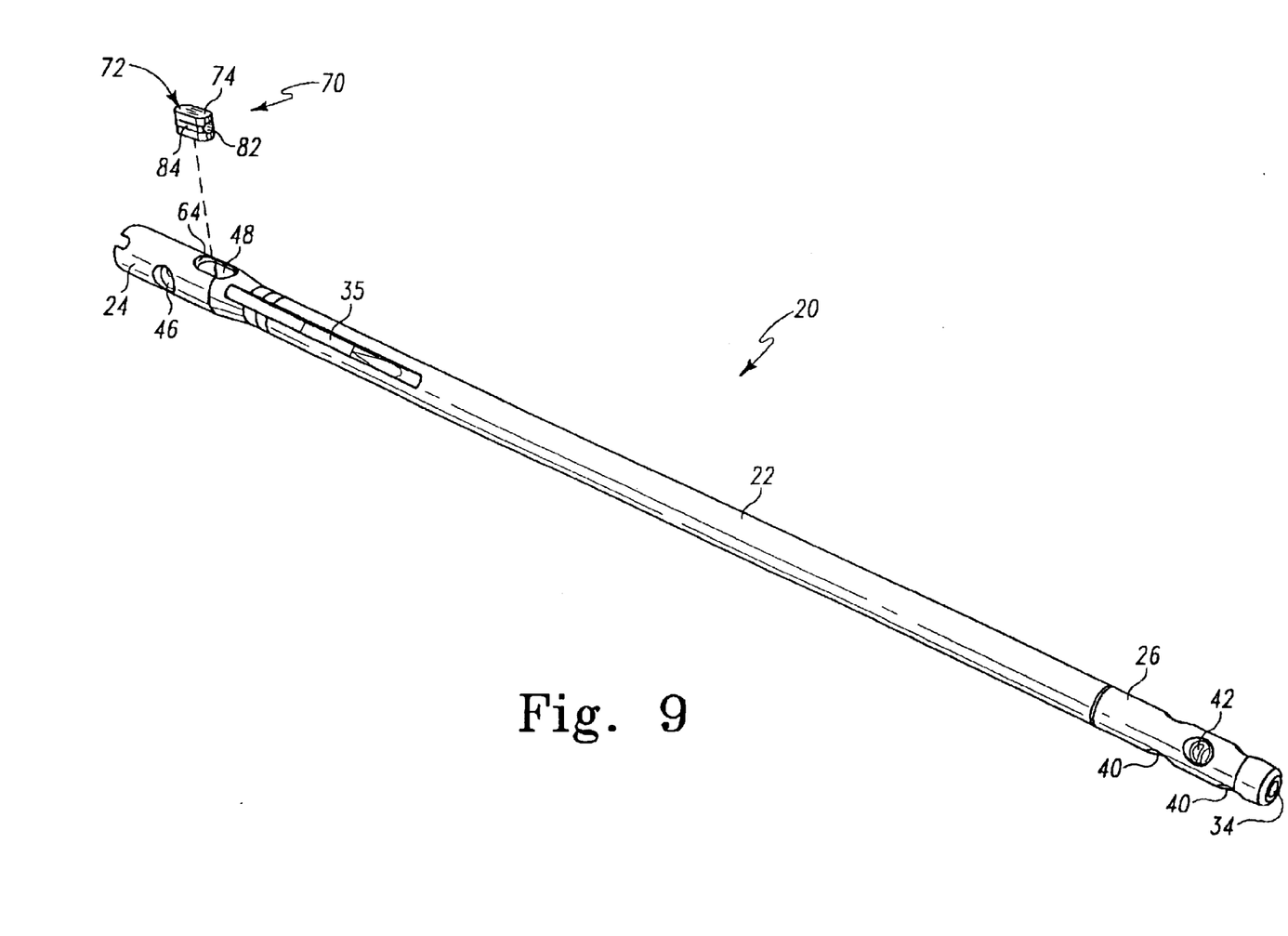
FIG. 9 is a perspective view of an exemplary intramedullary nail receiving an exemplary window insert in the dynamization opening of the intramedullary nail.

Referring to FIG. 9, the window insert 70 is shown being inserted into the intramedullary nail 20. Particularly, the window insert 70 is shown being inserted into the dynamization opening 48 of the intramedullary nail 20. This is accomplished before the intramedullary nail 20 is implanted into a patient. Also, it should be appreciated that while the intramedullary nail 20 has only one dynamization opening 48, the intramedullary nail 20 may have multiple dynamization openings both at the same end (proximal or distal), or both ends (proximal and distal).

Figure 10:
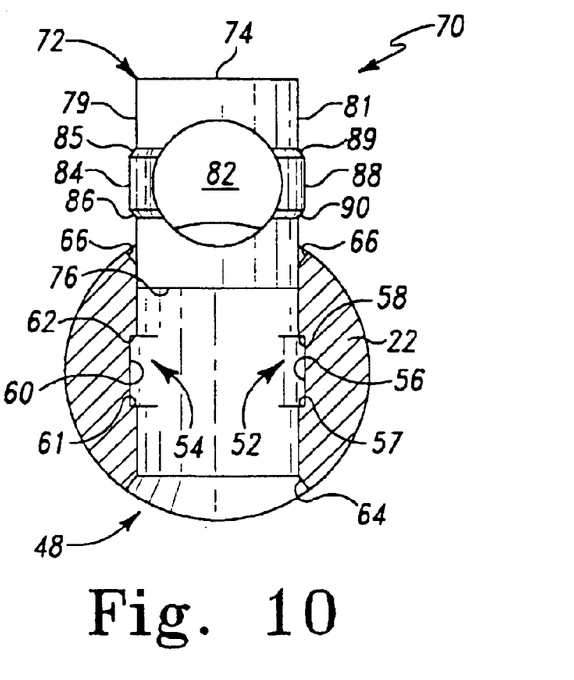
FIG. 10 is an enlarged sectional view of the intramedullary nail of FIG. 4B with the exemplary window insert being initially inserted into a dynamization opening of the intramedullary nail.
Figure 11:
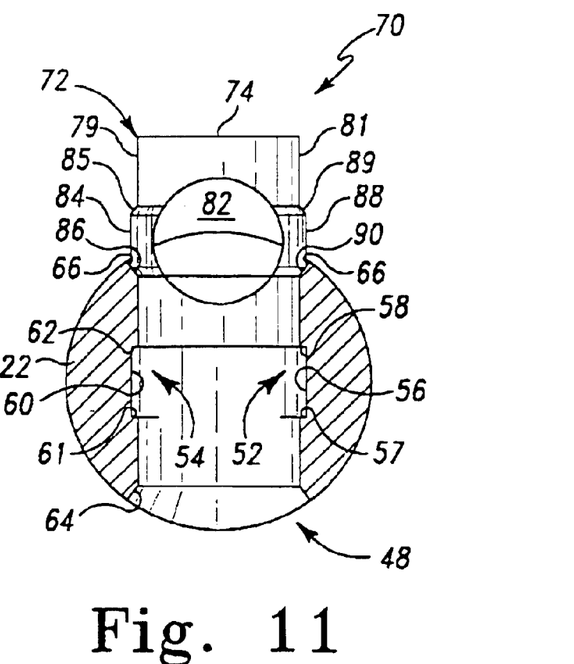
FIG. 11 is an enlarged sectional view of the intramedullary nail of FIG. 4B with the exemplary window insert being further inserted into the dynamization opening of the intramedullary nail.

Referring to FIGS. 10 and 11, the insertion of the window insert 70 into the dynamization opening 48 is depicted in greater detail. As the window insert 70 is initially placed into the dynamization opening 48 the angled surface 66 (or the angled surface 64 depending on the direction of insertion) guides the window insert 70 into the dynamization opening 48. The width of the window insert 70 (taken between the front surface 79 and the rear surface 81) is slightly less than the width of the dynamization opening 48. Such dimensions provide easy centering of the window insert 70 in the dynamization opening 48 with little to no canting of the window insert 70. Particularly, the window insert 70 slip fits into the dynamization opening 48 almost half way. This positions the window insert 70 true to the dynamization opening 48 (and the intramedullary nail 20) for final insertion.

The interference of the rails 84 and 88 lend itself to a spring action of the window insert 70 relative to the dynamization opening 48. Particularly, when angled surfaces 86 and 90 of the respective rails 84 and 88 reach the angled surface 66 of the dynamization opening 48 as shown in FIG. 11, the rails 84 and 88 (and thus the body 72) are/is thereafter compressed during further insertion into the dynamization opening 48. When the window insert 70 is in the position shown in FIG. 11, the angled surfaces 66 of the dynamization opening 48, 86 of the rail 84, and 90 of the rail 88, holds the window insert 70 in place until further insertion.

Further insertion of the window insert 70 seats the rails 84 and 88 in the respective channels 54 and 52. The square shoulders provided by the side walls 62, 61 and 57, 58 of the channels 54 and 52 respectively, allow the interference of the rails 84 and 88 to snap or expand into the respective channels 54 and 52. The square shoulders also help prevent the window insert 70 from being inserted past the center point of the dynamization opening 48.

Tests of the subject invention indicate an insertion force for the window insert 70 of approximately 200 pounds have been measured and are typical. A removal force, measured in tests of the subject invention, indicate a force of approximately 300 pounds are typical. While not shown, a tool may be used for insertion and removal of the window insert 70 after the intramedullary nail 20 is placed in the patient.

Because of the configuration of the window insert 70, the window insert 70 provides a spring type elastic fit in the dynamization opening 48. Such a spring type elastic fit provides an audio response and a snap feel when inserted. As well, the present configuration allows the window insert 70 to be press fit into the dynamization opening 48, is self-centering (of the window insert relative to the window insert opening), and provides increased resistance to removal.

The window insert 70 may be configured to provide a line-to-line interference fit with the dynamization opening 48 of the intramedullary nail 100. In this case, the opening 48 is configured with a first opening shape having a narrow portion adjacent an outer surface of the intramedullary nail 100, and a wider portion more interior the intramedullary nail 100. The window insert 70 has outer dimensions that correspond to the opening 48. Particularly, the window insert 70 has a first section that mates with the narrow portion of the opening 48, and a second section that is wider than the first section. The second section mates with the wider portion of the opening 48. The second section of the window insert is wider than the narrow portion of the opening 48 which serves to positively secure the window insert in the opening. Interference of the window insert may be on the order or 0.010 to 0.030 per side.

Figure 14:
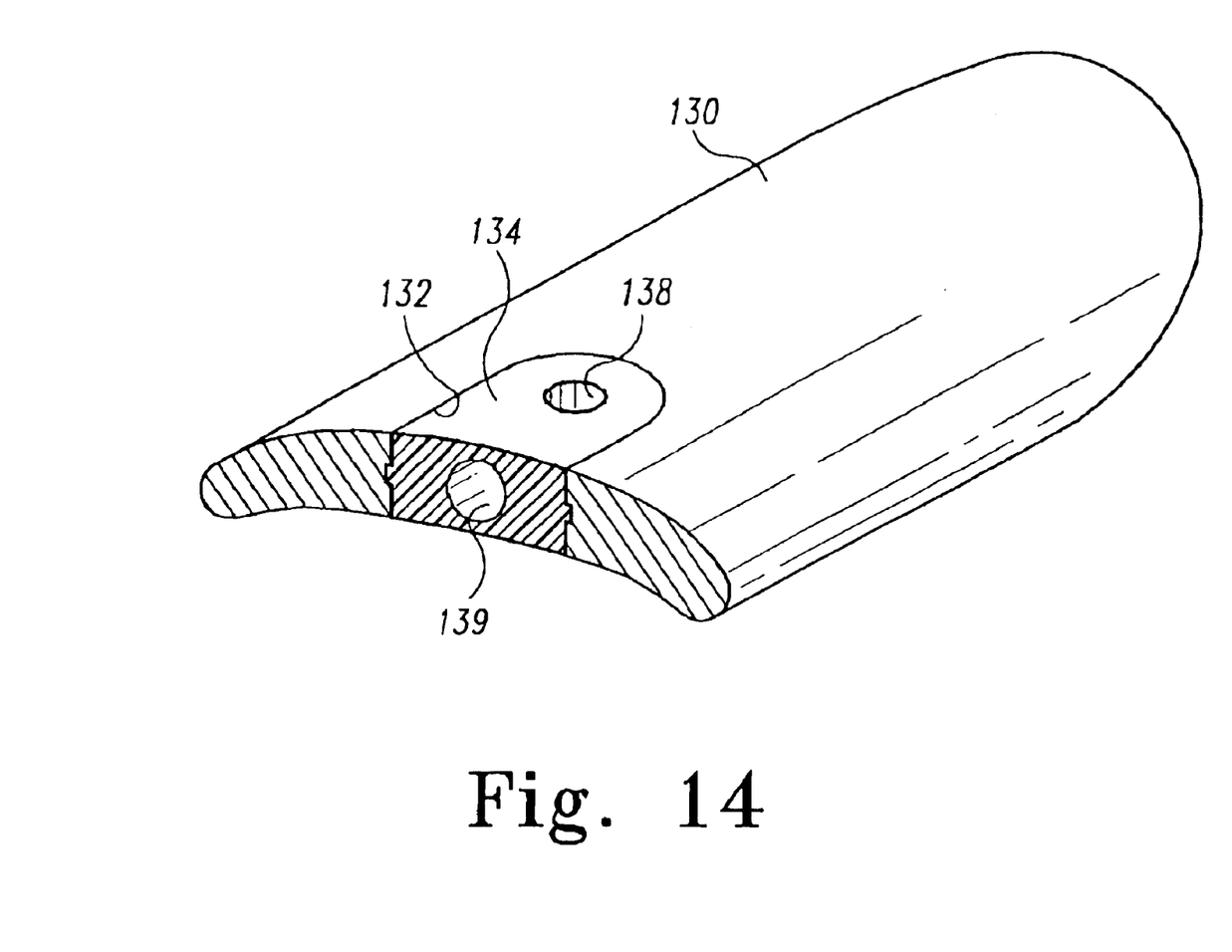
FIG. 14 is a sectional view of an exemplary bone plate or washer accommodating an exemplary window insert in accordance with the principles of the subject invention.

It should be appreciated that the subject invention may be utilized in various other bone holding/mending devices. Particularly, a dynamization window insert in accordance with the principles of the subject invention may be utilized with a bone holding/mending device that has a dynamization opening in accordance with the principles of the subject invention. In this regard, reference is made to FIG. 14. FIG. 14 depicts a bone plate, washer, or the like generally designated 130. The bone plate 130 may be made of a metal, a polymer, or other suitable material such as in known in the art for bone holding/mending devices.

The bone plate 130 has a dynamization opening 132 that is shaped in accordance with the principles presented herein, particularly such as that described above. A dynamization window insert 134 is received in the dynamization opening 132 in the same manner as that described above. The window insert 134 may be made from a bioresorbable or absorbable material or a non-resorbable/absorbable material such as that mentioned above and includes a longitudinal bore or cannula 139 and a lateral bore 138. The lateral bore 138 may be used to guide and/or allow a suture to extend therethrough. The bone plate 130 may be used in a manner known in the art.

Figure 15:
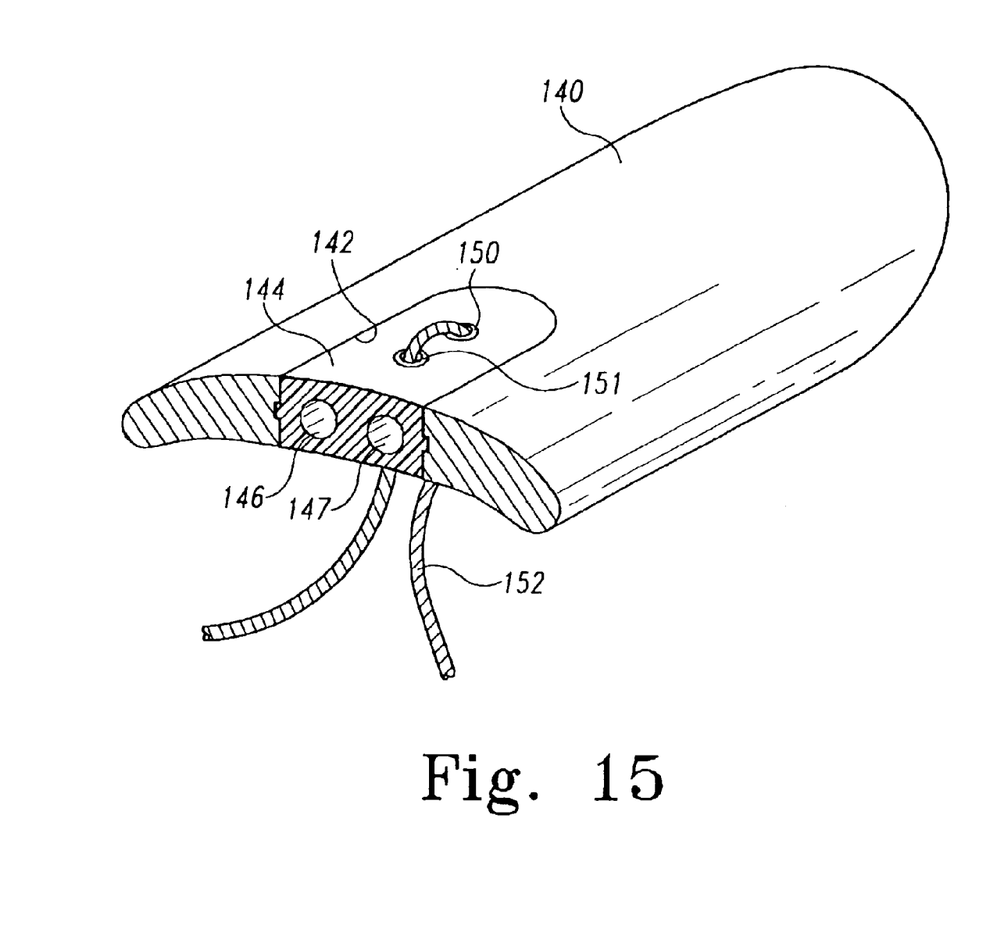
FIG. 15 is a sectional view of an exemplary bone plate or washer accommodating an exemplary window insert in accordance with the principles of the subject invention.

Referring to FIG. 15, there is depicted another bone plate, washer, or the like generally designated 140. The bone plate 140 may be made of a metal, a polymer, or other suitable material such as in known in the art for bone holding/mending devices. The bone plate 140 has a dynamization opening 142 that is shaped in accordance with the principles presented herein, particularly such as that described above. A dynamization window insert 144 is received in the dynamization opening 132 in the same manner as that described above. The window insert 144 may be made from a bioresorbable or absorbable material or a non-resorbable/absorbable material such as that mentioned above.

The window insert 144 includes two longitudinal bores or cannulas 146 and 147. As well, the window insert 144 has a first suture bore 150 and a second suture bore 151 each of which is laterally situated relative to the cannulas 146, 147. A suture 152 (rather than a bone fastener) is shown looped through the suture bores 150 and 151. The suture 152 would thereafter be used in a known manner. The preferably polymer material of the window insert 144 provides a cushion for the suture 152. Insertion and removal of the window insert 144 is accomplished as described above.

Use of the Subject Invention

A use of the subject invention will now be described. It should be appreciated, however, that the below-described use of the subject invention is only exemplary of one manner of use. Other manners of use not specifically described herein are contemplated. Referring to FIG. 12, there is depicted a cross section of a tibia that has been fractured into four bone fragments 102, 103, 104, and 105. An intramedullary nail 100 has been inserted in the medullary canal of the bone fragments 102, 103, 104, and 105. The intramedullary nail 100 thus holds the various bone fragments 102, 103, 104, and 105 in alignment for healing to take place. The intramedullary nail 100 has a first dynamization opening 110 in the distal end thereof and a second dynamization opening 112 in the proximate end thereof. The first and second dynamization openings 110 and 112 are configured as described above. The bone fragments 102, 103, 104, and 105 are aligned and drilled according to known procedures. The intramedullary nail 100 is inserted into the bone fragments 102, 103, 104, and 105 according to known procedures.

Referring to FIG. 13, the intramedullary nail 100 is shown in cross section after insertion through the various bone fragments 102, 103, 104, and 105. As well, only the proximal and distal ends of the intramedullary nail 100 are shown. Additionally, only the bone fragments 102 and 105 are shown. Before the placement of the intramedullary nail 100 through the bone fragments 102, 103, 104, and 105, a first dynamization window insert 120 is placed in the dynamization opening 110. The particular material of the window insert 120 is chosen by the surgeon. The window insert 120 has a cannula 121 that is aligned with a cannula 114 of the intramedullary nail 100. A second dynamization window insert 124 is placed in the dynamization opening 112. The particular material of the window insert 124 is chosen by the surgeon. The window insert 124 has a cannula 125 that is aligned with the cannula 114 of the intramedullary nail 100. It should be appreciated that the sequence of placement of the first and second window inserts 120 and 124 is arbitrary.

After placement of the first and second window inserts 120 and 124 into the intramedullary nail 100, and the placement of the intramedullary nail 100 into the bones/bone fragments, bone fasteners or screws 122 and 126 are driven through the respective bone fragment 102, 105, and into and through the respective window inserts 120, 124. The angle of placement of the bone fastener relative to its respective window insert and thus the longitudinal axis of the intramedullary nail 100, is variable and selected by the surgeon accordingly. In FIG. 13, the bone screw 122 is essentially perpendicular (90°) to the longitudinal axis of the window insert 120 and the intramedullary nail 100. The bone screw 126 is at an approximately 45° angle relative to the longitudinal axis of the window insert 124 and the intramedullary nail 100. The oval shape of the window inserts allow more room for cross screw placement and targeting of the screw. The placement of the screws as shown in FIG. 13 allows the bone fragments to shift during healing. Various deflections and/or stresses in the walls of the intramedullary nail and/or the window insert is limited through a design in accordance with the principles of the subject invention such as those set forth herein.

There are a plurality of advantages of the subject invention arising from the various features of the intramedullary nail and/or spacers therefor described herein. It will be noted that alternative embodiments of the intramedullary nail and/or spacer(s) of the subject invention may not include all of the features described yet still benefit from at least some of the advantages of such features. Those of ordinary skill in the art may readily devise their own implementations of an intramedullary nail that incorporate one or more of the features of the subject invention and fall within the sprit and scope of the subject invention.

What is claimed is:

1. An intramedullary nail for treatment of a fracture of a bone having a medullary canal extending longitudinally, comprising:
    a nail structure having a longitudinal nail body defining a distal end and a proximate end, said nail body having a dynamization opening in one of the distal end and the proximate end, said dynamization opening having a first interference receptor disposed in a wall of said dynamization opening and a second interference receptor disposed in said wall; and
    a window insert formed of a non-metal material and adapted to be inserted into said dynamization opening, said window insert having a window insert body having a first interference extending from a first surface of said window insert body and a second interference extending from a second surface of said window insert body, said first and second interferences adapted to be received in said first and second interference receptors of said dynamization opening respectively upon insertion of said window insert into said dynamization opening.

2. The intramedullary nail of claim 1, wherein the non-metal material comprises a bioresorbable material.

3. The intramedullary nail of claim 1, wherein the non-metal material comprises a polymer material.

4. The intramedullary nail of claim 1, wherein said first receptor comprises a first channel, and said second receptor comprises a second channel.

5. The intramedullary nail of claim 4, wherein said first and second channels each have a rectangular cross-section and said first and second interferences each include a chamfered surface extending from respective first and second surfaces.

6. The intramedullary nail of claim 1, wherein said first interference comprises a first rail extending a first distance from said first surface, and said second interference comprises a second rail extending a second distance from said second surface.

7. The intramedullary nail of claim 6, wherein said first distance is from 0.003 inches to 0.005 inches inclusive, and said second distance is from 0.003 inches to 0.005 inches inclusive.

8. The intramedullary nail of claim 1, wherein said first and second interference receptors are disposed on said wall diametrically opposite one another.

9. The intramedullary nail of claim 1, wherein said dynamization opening is dimensioned to compress said first and second Interferences upon initially receiving said window insert in said dynamization opening and to uncompress said first and second interferences upon further insertion of said window insert into said dynamization opening when said first and second interferences reach said first and second interference receptors respectively.

10. The intramedullary nail of claim 1, wherein said nail body has a second dynamization opening in one of the other of the distal end and the proximate end, said second dynamization opening having a first interference receptor disposed in a wall of said second dynamization opening and a second interference receptor disposed in said wall; and
    a second window insert formed of a non-metal material and adapted to be inserted into said second dynamization opening, said second window insert having a window insert body having a first interference extending from a first surface of said window insert body and a second interference extending from a second surface of said window insert body, said first and second interferences adapted to be received in said first and second interference receptors of said second dynamization opening respectively upon insertion of said second window insert into said second dynamization opening.

11. The intramedullary nail of claim 10, wherein said first receptor of said second dynamization opening comprises a first channel, and said second receptor of said second dynamization opening comprises a second channel.

12. The intramedullary nail of claim 11, wherein said first and second channels of said second dynamization opening each have a rectangular cross-section and said first and second interferences of said second window insert body each include a chamfered surface extending from respective first and second surfaces thereof.

13. The intramedullary nail of claim 10, wherein said first interference of said second window insert comprises a first rail extending a first distance from said first surface thereof, and said second interference of said second window insert comprises a second rail extending a second distance from said second surface thereof.

14. The intramedullary nail of claim 13, wherein said first distance of said first rail of said second window insert is from 0.003 inches to 0.005 inches inclusive, and said second distance of said second rail of said second window insert is from 0.003 inches to 0.005 inches inclusive.

15. The intramedullary nail of claim 10, wherein said first and second interference receptors of said second dynamization opening are disposed on said wall diametrically opposite one another.

16. The intramedullary nail of claim 10, wherein said second dynamization opening is dimensioned to compress said first and second interferences of said second window insert upon initially receiving said second window insert in said second dynamization opening and to uncompress said first and second interferences of said second window insert upon further insertion of said second window insert into said second dynamization opening when said first and second interferences of said second window insert reach said first and second interference receptors of said second dynamization opening respectively.

17. An intramedullary nail for treatment of a fracture of a bone having a medullary canal extending longitudinally, comprising:
   a longitudinal nail body defining a distal end and a proximate end, said nail body having a dynamization opening extending through said nail body at one of said distal end and said proximate end essentially transverse to a longitudinal axis of said nail body, said dynamization opening defined by an oval wall, said oval wall having a first groove positioned essentially parallel to said longitudinal axis and a second groove disposed diametrically opposite said first groove and essentially parallel to said longitudinal axis; and
   a dynamization window insert formed of a non-metal material and adapted to be inserted into said dynamization opening, said window insert having an oval window insert body having a first rail extending a first distance from a first surface of said window insert body and a second rail extending a second distance from a second surface of said window insert body, said first and second rails adapted to be received in said first and second grooves of said dynamization opening respectively upon insertion of said dynamization window insert into said dynamization opening.

18. The intramedullary nail of claim 17, wherein the non-metal material comprises a bioresorbable material.

19. The intramedullary nail of claim 17, wherein the non-metal material comprises a polymer material.

20. The intramedullary nail of claim 17, wherein said first distance is from 0.003 inches to 0.005 inches inclusive, and said second distance is from 0.003 inches to 0.005 inches inclusive.

21. The intramedullary nail of claim 17, wherein said dynamization opening is dimensioned to compress said first and second rails upon initially receiving said dynamization window insert in said dynamization opening and to uncompress said first and second rails upon further insertion of said dynamization window insert into said dynamization opening when said first and second rails reach said first and second grooves respectively.

22. The intramedullary nail of claim 17, wherein said nail body has a second dynamization opening extending through said nail body at the other of said distal end and said proximate end and essentially transverse to a longitudinal axis of said nail body, said second dynamization opening defined by an oval wall, said oval wall having a first groove positioned essentially parallel to said longitudinal axis and a second groove disposed diametrically opposite said first groove and essentially parallel to said longitudinal axis; and
   a second dynamization window insert formed of a non-metal material and adapted to be inserted into said second dynamization opening, said second window insert having an oval window insert body having a first rail extending a first distance from a first surface of said window insert body and a second rail extending a second distance from a second surface of said window insert body, said first and second rails adapted to be received in said first and second grooves of said second dynamization opening respectively upon insertion of said second dynamization window insert into said second dynamization opening.

23. The intramedullary nail of claim 22, wherein said first and second grooves of said second dynamization opening each have a rectangular cross-section and said first and second rails of said second window insert body each include a chamfered surface extending from respective first and second surfaces thereof.

24. The intramedullary nail of claim 22, wherein said first distance of said first rail of said second window insert is from 0.003 inches to 0.005 inches inclusive, and said second distance of said second rail of said second window insert is from 0.003 inches to 0.005 inches inclusive.

25. The intramedullary nail of claim 22, wherein said second dynamization opening is dimensioned to compress said first and second rails of said second window insert upon initially receiving said second window insert in said second dynamization opening and to uncompress said first and second interferences of said second window insert upon further insertion of said second window insert into said second dynamization opening when said first and second interferences of said second window insert reach said first and second grooves of said second dynamization opening respectively.

26. A window insert for a dynamization opening of an intramedullary nail comprising:
   an oval body defining a top and bottom surface, a first and second side surface, and a first and second curved side;
   a first rail disposed on said first side and extending a first distance therefrom; and
   a second rail disposed on said second side and extending a second distance therefrom,
   wherein said body further includes a cannula.

27. A method of retaining bone fragments comprising the steps of:
   placing a dynamization window insert in a dynamization opening of an intramedullary nail, the intramedullary nail having a longitudinal nail body defining a distal end and a proximate end, said dynamization opening extending through said nail body at one of said distal end and said proximate end essentially transverse to a longitudinal axis of said nail body, said dynamization opening defined by an oval wall, said oval wall having a first groove positioned essentially parallel to said longitudinal axis and a second groove disposed diametrically opposite said first groove and essentially parallel to said longitudinal axis, the dynamization window insert formed of a non-metal material and adapted to be inserted into said dynamization opening, said window insert having an oval window insert body having a first rail extending a first distance from a first surface of said window insert body and a second rail extending a second distance from a second surface of said window insert body, said first and second rails adapted to be received in said first and second grooves of said dynamization opening respectively upon insertion of said dynamization window insert into said dynamization opening;
   placing the intramedullary nail through the bone fragments, and inserting a bone fastener through the dynamization window insert.

28. A bone support assembly for treatment of a bone, the bone support assembly comprising:
   a bone support implant formed of a non-resorbable material, said bone support implant having a first opening defined therein, said first opening having a first opening shape including a narrow portion adjacent an outer surface of said bone support implant and a wider portion more interior the bone support implant; and a first window insert formed of a non-metal material, said first window insert having outer dimensions that correspond to said first opening, said first window insert having a first section that mates with said narrow portion of said first opening, said first window insert having a second section wider than said first section that mates with said wider portion of said first opening more interior of said bone support implant, wherein said second section of said first window insert is wider than said narrow portion of said first opening and serves to positively secure said first window insert in said first opening with an interference fit.

* * * * *